United States Patent
Ledwosinska et al.

(10) Patent No.: US 9,696,272 B2
(45) Date of Patent: Jul. 4, 2017

(54) SYSTEMS AND METHODS FOR HUMIDITY MEASUREMENT USING DIELECTRIC MATERIAL-BASED RELATIVE HUMIDITY SENSORS

(71) Applicant: Silicon Laboratories Inc., Austin, TX (US)

(72) Inventors: Elzbieta A. Ledwosinska, Austin, TX (US); John C. Gammel, Round Rock, TX (US); William H. Simcoe, Austin, TX (US)

(73) Assignee: Silicon Laboratories Inc., Austin, TX (US)

( * ) Notice: Subject to any disclaimer, the term of this patent is extended or adjusted under 35 U.S.C. 154(b) by 140 days.

(21) Appl. No.: 14/821,351

(22) Filed: Aug. 7, 2015

(65) Prior Publication Data
US 2017/0038327 A1   Feb. 9, 2017

(51) Int. Cl.
*G01N 27/22* (2006.01)

(52) U.S. Cl.
CPC ......... *G01N 27/225* (2013.01); *G01N 27/228* (2013.01)

(58) Field of Classification Search
CPC ... G01N 25/56; G01N 27/223; G01N 33/0006
See application file for complete search history.

(56) References Cited

U.S. PATENT DOCUMENTS

| | | | | |
|---|---|---|---|---|
| 6,437,582 B1 * | 8/2002 | Rode | ............... | A01D 41/1277 |
| | | | | 324/658 |
| 6,564,633 B2 * | 5/2003 | Stormbom | ......... | G01N 27/223 |
| | | | | 73/1.06 |
| 7,030,630 B2 * | 4/2006 | Haas | .................... | G01N 27/223 |
| | | | | 324/664 |
| 7,032,448 B2 * | 4/2006 | Hamamoto | ......... | G01N 27/225 |
| | | | | 361/280 |
| 7,077,004 B2 * | 7/2006 | Mitter | ................ | G01N 27/223 |
| | | | | 73/29.01 |

(Continued)

OTHER PUBLICATIONS

Stephins et al., "Measuring Capacitor Parameters using Vector Network Analyzers", Electronics vol. 18, No. 1, Jun. 2014, 10 pgs.

(Continued)

*Primary Examiner* — David A Rogers
(74) *Attorney, Agent, or Firm* — Egan, Peterman, Enders & Huston, LLP.

(57) ABSTRACT

Systems and methods are provided that may be implemented to improve accuracy of relative humidity (RH) determination from dielectric sensing material-based RH sensors, e.g., by decreasing shift and drift effects and compensating for dielectric material aging to improve RH sensor accuracy. The disclosed systems and methods may be implemented to improve RH sensing accuracy by correcting humidity-sensitive electrical parameters (e.g., capacitance, effective resistance, etc.) based on other other measured sensor electrical operating characteristics (e.g., such as real time sensor circuit phase angle) and/or selection of sensor electrical parameters (e.g., such as optimized operating frequency) that are employed for sensing changes in dielectric constant of a dielectric material-based RH sensor.

25 Claims, 9 Drawing Sheets

(56) References Cited

U.S. PATENT DOCUMENTS

| | | | | |
|---|---|---|---|---|
| 7,181,966 B2* | 2/2007 | Isogai | ............... | G01N 27/223 |
| | | | | 326/105 |
| 7,719,290 B2* | 5/2010 | Nikolaus | ............ | G01N 27/228 |
| | | | | 324/667 |
| 7,730,759 B2* | 6/2010 | Rombach | ............ | G01N 25/56 |
| | | | | 73/1.59 |
| 8,007,167 B2 | 8/2011 | Cummins | | |
| 8,030,949 B2* | 10/2011 | Gotz | ................ | G01N 27/223 |
| | | | | 324/664 |
| 8,149,003 B2* | 4/2012 | Koch | ................ | G01N 27/223 |
| | | | | 324/547 |
| 2008/0024110 A1* | 1/2008 | Nikolaus | ............ | G01N 27/228 |
| | | | | 324/71.1 |
| 2010/0109635 A1* | 5/2010 | Gotz | ................ | G01N 27/223 |
| | | | | 324/71.1 |
| 2014/0026642 A1 | 1/2014 | O'Connell | | |
| 2014/0026653 A1 | 1/2014 | Del Signore et al. | | |

OTHER PUBLICATIONS

Ralston et al., "A Model for the Relative Environmental Stability of a Series of Polyimide Capacitance Humidity Sensors", Sensors and Actuators B34, 1996, 6 pgs.
Matsuguchi et al., "Draft Phenomenon of Capacitive-Type Relative Humidity Sensors in a Hot and Humid Atmosphere", Journal of the Electrochemical Society, 147, 2000, 4 pgs.
Eder et al., "A CMOS Smart Temperature and Humidity Sensor With Combined Readout", Sensors, 2014, 20 pgs.

* cited by examiner

SYSTEMS AND METHODS FOR HUMIDITY MEASUREMENT USING DIELECTRIC MATERIAL-BASED RELATIVE HUMIDITY SENSORS

FIELD OF THE INVENTION

This disclosure generally relates to relative humidity sensors and, more particularly, to dielectric material-based sensors utilized for measuring relative humidity.

BACKGROUND

A capacitive sensor is one type of sensor that is employed for measuring relative humidity (RH) concentrations in ambient air. FIG. 1 illustrates a cross-section of a conventional capacitive sensor 100 that is used for measuring RH. As shown in FIG. 1, spaced sensor electrodes 102, 104 and 106 are formed on a substrate 101 as the "fingers" of an interdigitated capacitive structure, although conventional capacitive sensors have also employed parallel-plate capacitor configurations. It will be recognized that the capacitive structure may be formed by many electrodes arranged as shown in FIG. 1. Capacitance of sensor 100 increases with RH due to absorption of high polarity water molecules. Generally the water molecules can be absorbed and desorbed. Thus, capacitance measurements obtained between the electrodes may be utilized to determine increasing and decreasing relative humidity levels. Sensor electrodes may be any of a wide variety of conductive materials. Substrate 101 may be any of a wide variety of substrates and may be in one non-limiting example a semiconductor substrate that includes a wide variety of integrated circuit layers (not shown) as is known in the art. For example, U.S. Pat. No. 8,007,167 to Cummins, the disclosure of which is expressly incorporated herein by reference, provides a capacitive sensor formed on an integrated circuit substrate.

The sensor electrodes may be covered by a passivation layer 103 and further overlaid with a sensing layer 105 of polyimide. Alternatively, sensing layer 105 may be utilized without the inclusion of a passivation layer 103. In operation, the sensing layer 105 is exposed to the ambient conditions under which a measurement is desired. Thus, at least a portion of the upper surface of the sensing layer 105 may be an air/dielectric layer interface and layer 105 may be considered an ambient condition humidity-sensitive layer. Capacitive RH sensors 100 such as illustrated in FIG. 1 are typically provided in a package with an opening defined in the package that is provided for allowing ingress of ambient air or other gas into the package.

Still referring to FIG. 1, concentration of water vapor in the ambient air impacts (and changes) the dielectric constant of the sensing layer 105 as differing concentrations of water vapor in the ambient air will impact the amount of ingress of water molecules into the sensor dielectric material of sensing layer 105. Thus, by measuring the capacitance between the electrodes the RH concentrations in the ambient air may be inferred. As shown in FIG. 1, the electric fields between the electrodes may include fields 110a contained in the passivation layer 103, fields 110b which pass in part through the sensing layer 105, and other parasitic fields (not shown). In operation, changes in capacitance of sensor 100 due to changes in the dielectric constant of the sensing layer 105 are utilized to detect the ambient RH conditions. However, various components of the capacitive measurement may be impacted by several factors, i.e., such as temperature changes, chemical contaminants, physical contaminants, etc. These factors thus impact the accuracy of the detection of the ambient RH conditions using sensor 100.

Polyimide-based capacitive RH sensors also suffer from stability problems as they age at conditions of elevated humidity and temperature. This results in decreasing RH sensor accuracy upon subjection of a polyimide capacitive RH sensor to high temperature and humidity environments over time. With exposure to elevated humidity and temperature levels the measured capacitance (sensor response) obtained from a polyimide-based capacitive RH sensor slowly drifts with time above the reference capacitance value that corresponds to actual environmental RH conditions, and that should be exhibited by the sensor in the absence of the effects of temperature and humidity. This causes the aged sensor to indicate a false increase in RH that is referred to as "drift". A related term is "shift", which is the similar difference in sensor response reading at non-elevated ambient humidity and temperature conditions following a high RH exposure. It has been proposed to select or alter the chemical properties of a polyimide for increased stability at high temperature and humidity in an attempt to improve accuracy of capacitive RH sensors after exposure to elevated temperature and humidity.

SUMMARY

Disclosed herein are systems and methods that may be implemented to improve accuracy of relative humidity (RH) determination from dielectric material-based RH sensors, e.g., by decreasing shift and drift effects and compensating for material aging of a dielectric material of a RH sensor to improve RH sensor accuracy. Unlike conventional solutions that rely on selecting or altering the chemical properties of a polyimide sensing material, the disclosed systems and methods may instead be implemented to achieve improvement in RH sensing accuracy by correcting humidity-sensitive electrical parameters (e.g., such as capacitance, effective resistance, etc.) that are used to sense changes in dielectric constant of a sensor dielectric material (e.g., such as layer) to determine values of RH. In the practice of the disclosed systems and methods, such humidity-sensitive electrical parameters (e.g., capacitance, effective resistance, etc.) may be corrected based on other measured sensor electrical operating characteristics (e.g., such as real time sensor circuit phase angle) and/or by selection of sensor electrical measurement parameters (e.g., such as optimized operating frequency) that are employed for sensing changes in dielectric constant of a dielectric material-based RH sensor. The disclosed systems and methods may be advantageously implemented to improve accuracy of relative humidity (RH) determination from RH sensors that employ any type of dielectric material as a RH sensing material (e.g., as a dielectric material layer or other suitable physical or geometric configuration of dielectric material) that absorbs water and exhibits a measurable change in dielectric constant as a result thereof. Examples of such dielectric sensing materials include, but are not limited to, polyimides as well as non-polyimide polymers like acrylic polymers, acrylates, polycarbonates, silicon based polymers such as polysiloxanes, etc.

In one exemplary embodiment, the disclosed systems and methods may be implemented in a manner that achieves a humidity-sensing accuracy improvement that is entirely based on sensor electrical operating characteristics and/or sensor electrical measurement parameters that are used in the measurement of humidity-sensitive electrical parameters from a dielectric material-based RH sensor, i.e., to provide a non-chemical solution for humidity-sensing performance improvement. In a further embodiment, the disclosed systems and methods may be so implemented as an on-chip solution to achieve performance improvement for polymer-based RH sensors that are formed on an integrated circuit that itself includes circuitry, processing device/s, memory and the like configured to provide relative humidity readings based upon detected changes in dielectric constant of an on-chip humidity-sensitive polymer (e.g., configured as a polymer sensing layer).

In one exemplary embodiment, the disclosed systems and methods may be implemented to operate a dielectric material-based RH sensor at an optimized measurement frequency that is selected to minimize drift and shift effects on the measured humidity-sensitive electrical parameter values (e.g., such as capacitance or effective resistance) obtained from the RH sensor. Such an optimized measurement frequency may be determined based on empirical measurements made during device characterization of the RH sensor, and may be programmed into memory for use by a processing device/s that is configured to both control frequency of RH sensor operation and to calculate RH in real time based on changes in a sensor humidity-sensitive electrical parameter (e.g., such as capacitance or effective resistance) value with time. In one exemplary embodiment, such an optimized frequency may be equal to greater than a minimum operating frequency that has been selected based on sensor device characterization, and that is increased relative to conventional capacitive sensor operating frequency.

In another exemplary embodiment, the disclosed systems and methods may be implemented to correct RH measurements obtained from a dielectric material-based RH sensor to correct for sensor aging based on a current (e.g., real time or recent) measured phase angle ($\phi$) of the sensor circuit (e.g., by measuring a series resistance component $\phi$-based on the capacitive sensor circuit) at one or more frequencies. For example, a RH measurement calculated from RH sensor capacitance may be corrected based on a determined difference in phase angle ($\Delta\phi$) between a value of $\phi$ measured at a given oscillator frequency or alternating current (AC) frequency prior to any or substantially any sensor exposure to humidity ($\phi_{pre-exposure}$) and a value of $\phi$ measured at a given frequency after some sensor exposure to humidity ($\phi_{post-exposure}$). In this regard, change in phase angle ($\Delta\phi$) may be used in one embodiment as an indicator of prior high RH exposure, and as a basis for an amount of correction to be applied to the current real time calculated RH value.

It will be understood that a pre-exposure value of $\phi$ ($\phi_{pre-exposure}$) may be made measured prior to any or substantially any sensor exposure to humidity (e.g., when a un-aged sensor dielectric material possesses an original $\phi$ that is near or about $-90°$), or may be alternatively measured after some exposure to humidity that is less than the current sensor exposure to humidity ($\phi_{post-exposure}$). For example exposure to some humidity level (e.g., less than or equal to about 50% RH) for a relatively short period of time (e.g., less than or equal to about 40 hours) may have relatively small effect on the original phase angle and values of shift and drift, while longer exposure (e.g., greater than about 40 hours) to a relatively higher humidity level (e.g., greater than about 50% relatively humidity) may have a relatively larger effect on the phase angle and values of shift and drift. An example of this effect is illustrated in FIG. 5 described further herein, it being understood that higher humidity exposures for relatively shorter periods of time, and lower humidity exposures for relatively longer periods of time, may each have negligible effects (e.g. less than about 10% of original phase angle value) on phase angle, such that a characterization such as illustrated in FIG. 5 may be used in one embodiment to differentiate between pre-exposure and post-exposure conditions of a given dielectric sensing material.

Advantageously, the disclosed systems and methods may be implemented in a further embodiment to provide a two-fold mechanism to improve dielectric material-based RH sensor accuracy by both operating the sensor at an optimized (e.g., increased) frequency to minimize drift, while at the same time correcting RH measurements obtained from the RH sensor using a correction factor (X) that is based on measured phase angle to compensate for sensor aging (e.g., prior exposure to relative high levels of humidity and at relative high temperatures relative to ambient room temperature conditions of humidity and temperature).

The disclosed systems and methods may be implemented with a variety of dielectric material-based capacitive RH sensor configurations including, but not limited to, packaged integrated circuit configurations having active circuitry that underlies dielectric material-based RH capacitive sensor circuitry that is aligned with (e.g., positioned underneath) a package opening that allows ingress of ambient air or other gas into the package.

In one respect, disclosed herein is a method of operating a relative humidity (RH) sensor to measure RH conditions. The method may include selecting an initial test measurement frequency as a current selected test measurement frequency for a humidity-sensitive dielectric material of the RH sensor. The method may further include then: a) exposing a humidity-sensitive dielectric material of the RH sensor to at least one value of RH while applying the current selected test measurement frequency to the humidity-sensitive dielectric material of the RH sensor; b) using at least one processing device to measure a humidity-sensitive electrical parameter value of the RH sensor at the exposed value of RH while applying the current selected test measurement frequency to the humidity-sensitive dielectric material of the RH sensor; c) using at least one processing device to determine a value of sensor shift (S) and/or sensor drift (D) at the current selected test measurement frequency by comparing the measured humidity-sensitive electrical parameter value to a baseline humidity-sensitive electrical parameter value previously measured at the same value of RH humidity; d) selecting at least one new and different test measurement frequency as the current selected test measurement frequency and iteratively repeating steps a) to d) for at least one additional time with the new current selected test measurement frequency; and then e) using at least one processing device to determine an operating humidity measurement frequency based at least in part on the values of S and/or D determined at previously-selected different test frequencies during multiple iterations of steps a) to d).

In another respect, disclosed herein is a method of operating a relative humidity (RH) sensor to measure RH conditions with a humidity-sensitive dielectric material of the RH sensor. The method may include: exposing a humidity-sensitive dielectric material of the RH sensor to a first humidity value while applying an operating humidity measurement frequency to the humidity-sensitive dielectric material of the RH sensor; using at least one processing device to measure a humidity-sensitive electrical parameter value of the humidity-sensitive dielectric material while exposed to the first humidity value and while applying the operating humidity measurement frequency to the humidity-sensitive dielectric material of the RH sensor; and using at least one processing device to correct the measured humidity-sensitive electrical parameter value of the humidity-sensitive dielectric material based on a determined difference in phase angle phase angle ($\Delta\phi$) between a post-exposure phase angle ($\phi_{post\text{-}exposure}$) of a circuit applying a phase angle measurement frequency to the humidity-sensitive dielectric material and a predetermined pre-exposure phase angle ($\phi_{pre\text{-}exposure}$), the predetermined pre-exposure phase angle ($\phi_{pre\text{-}exposure}$) being measured prior to measurement of the post-exposure phase angle ($\phi_{post\text{-}exposure}$). The operating humidity measurement frequency and the phase angle measurement frequency may either be the same or different frequencies.

In another respect, disclosed herein is a semiconductor circuit device, including at least one processing device configured to be coupled to humidity-sensitive dielectric material of a relative humidity (RH) sensor, the processing device being programmed to receive and measure a humidity-sensitive electrical parameter value signal that is produced from the humidity-sensitive dielectric material in response to application of a humidity measurement frequency to the humidity-sensitive dielectric material, and to produce a relative humidity (RH) output signal based on the humidity-sensitive electrical parameter value signal. The RH output signal is representative of a value of RH to which the humidity-sensitive dielectric material is currently exposed. The processing device may be further programmed to: a) measure a humidity-sensitive electrical parameter value of the RH sensor at an exposed value of RH while a current selected test measurement frequency is applied to the humidity-sensitive dielectric material of the RH sensor; b) determine a value of sensor shift (S) and/or sensor drift (D) at the current selected test measurement frequency by comparing the measured humidity-sensitive electrical parameter value to a baseline humidity-sensitive electrical parameter value previously measured at the same value of RH humidity; c) iteratively repeat steps a) and b) for at least one additional time at a new current selected test measurement frequency that is different from the previous current selected test measurement frequency; and then d) determine an operating humidity measurement frequency based at least in part on the values of S and/or D determined at previously-selected different test frequencies during multiple iterations of steps a) and b).

In another respect, disclosed herein is a semiconductor circuit device, including at least one processing device configured to be coupled to humidity-sensitive dielectric material of a relative humidity (RH) sensor, the processing device being programmed to receive and measure a humidity-sensitive electrical parameter value signal that is produced from the humidity-sensitive dielectric material in response to application of a measurement frequency to the humidity-sensitive dielectric material, and to produce a relative humidity (RH) output signal based on the humidity-sensitive electrical parameter value signal. The RH output signal is representative of a value of RH to which the humidity-sensitive dielectric material is currently exposed; and the processing device may be further programmed to: measure a humidity-sensitive electrical parameter value of the humidity-sensitive dielectric material while exposed to a first humidity value and while applying an operating humidity measurement frequency to the humidity-sensitive dielectric material of the RH sensor; measure a post-exposure phase angle ($\phi_{post\text{-}exposure}$) of a circuit applying a phase angle measurement frequency to the humidity-sensitive dielectric material; determine a difference in phase angle phase angle ($\Delta\phi$) between a post-exposure phase angle ($\phi_{post\text{-}exposure}$) of a circuit applying a phase angle measurement frequency to the humidity-sensitive dielectric material and a predetermined pre-exposure phase angle ($\phi_{pre\text{-}exposure}$) that is measured prior to measurement of the post-exposure phase angle ($\phi_{post\text{-}exposure}$); and correct the measured humidity-sensitive electrical parameter value of the humidity-sensitive dielectric material based on a determined difference in phase angle phase angle ($\Delta\phi$) between the post-exposure phase angle ($\phi_{post\text{-}exposure}$) and the predetermined pre-exposure phase angle ($\phi_{pre\text{-}exposure}$). The operating humidity measurement frequency and the phase angle measurement frequency may either be the same or different frequencies.

In the practice of the disclosed systems and methods, it will thus be understood that in one embodiment a dielectric material-based RH sensor may be operated to produce a relative humidity (RH) output signal that is based on a humidity-sensitive electrical parameter value signal measured at an optimized operating frequency selected using multiple iterations of different test frequencies as described above, and that has been corrected based on based on a determined difference in phase angle phase angle ($\Delta\phi$) between a post-exposure phase angle ($\phi_{post\text{-}exposure}$) and a predetermined pre-exposure phase angle ($\phi_{pre\text{-}exposure}$) of a circuit applying a phase angle measurement frequency to the humidity-sensitive dielectric material. In another embodiment, it is possible that a humidity-sensitive electrical parameter (e.g., such as capacitance or effective resistance) and phase angle change ($\Delta\phi$) may be analyzed at multiple different test measurement frequency points to make the correction less sensitive to other variables such as process and temperature. In another embodiment, a humidity-sensitive electrical parameter (e.g., such as capacitance or effective resistance) may be measured at one operating measurement frequency for determining RH humidity (e.g., that is optimum for RH determination), while post-exposure phase angle ($\phi_{post\text{-}exposure}$) and/or pre-exposure phase angle ($\phi_{pre\text{-}exposure}$) may be each or both be measured angle at different measurement frequencies than the operating measurement frequency used for determining RH humidity. In yet another embodiment, either one or both of phase angle change ($\Delta\phi$) measurements and humidity-sensitive electrical parameter (e.g., such as capacitance or effective resistance) may be measured at multiple different measurement frequencies.

DESCRIPTION OF ILLUSTRATIVE EMBODIMENTS

Figure 2:
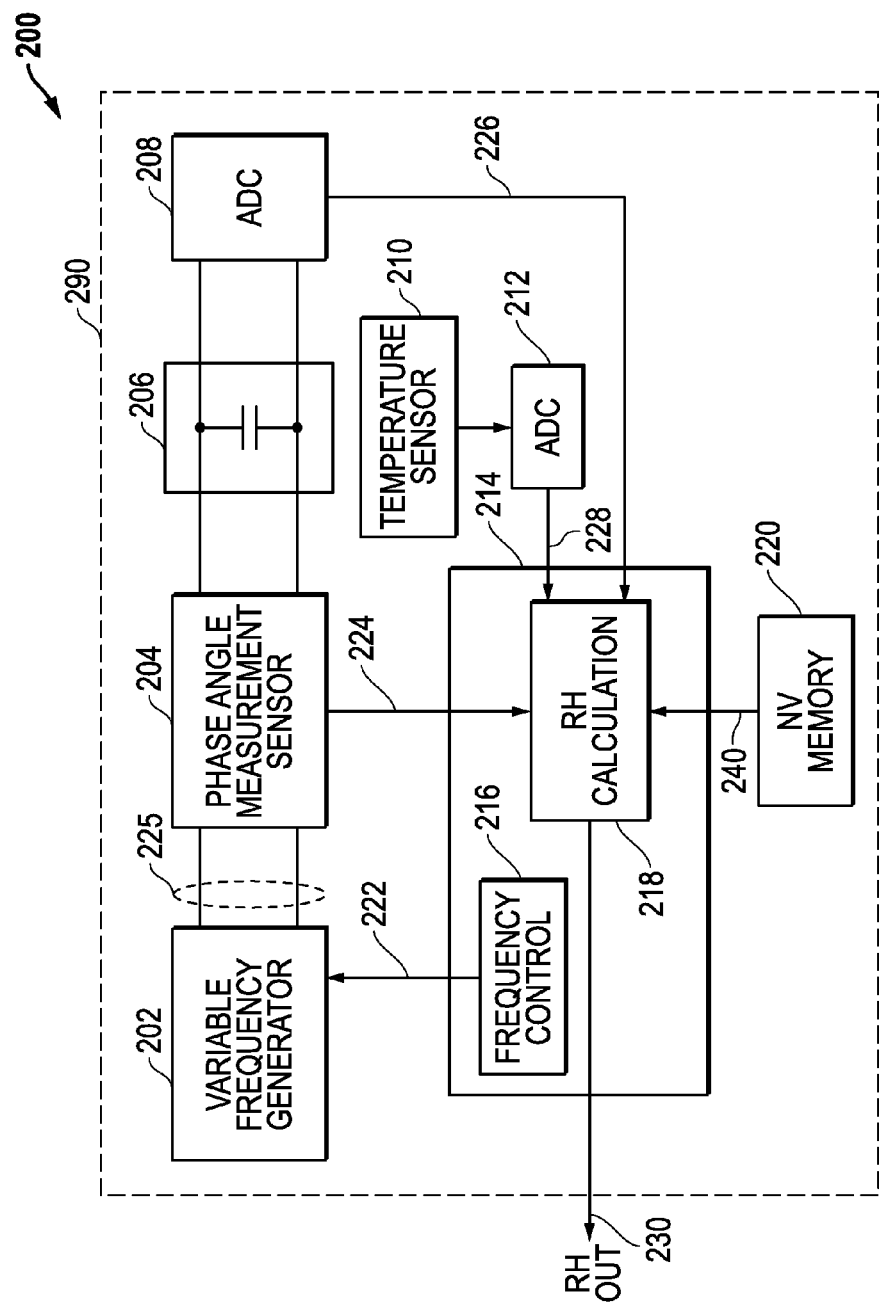
FIG. 2 illustrates a simplified block diagram of relative humidity sensor system according to one exemplary embodiment of the disclosed systems and methods.

FIG. 2 illustrates a simplified block diagram of RH sensor system 200 that is configured to sense RH value in real time based upon detected changes in capacitance of a dielectric material-based capacitive RH sensor 206, and to produce a RH output signal 230 representative of RH. Although FIG. 2 illustrates a RH sensor system 200 utilizing a dielectric material-based capacitive RH sensor 206, it will be understood that the disclosed systems and methods may be implemented with dielectric material-based RH sensor systems that utilize other types of humidity-sensitive electrical parameters (e.g., such as effective resistance) to produce a RH output signal that is based on changes in dielectric constant of a dialectic material with changing RH.

In one exemplary embodiment, the illustrated components of RH sensor system 200 may optionally be all integrated within or on a single semiconductor integrated circuit chip 290, e.g., which may itself be provided within a semiconductor package having one or more openings defined in the package to allow ingress of ambient air or other gas into the package so as to contact capacitive RH sensor 206. In a further embodiment, active circuitry components of RH sensor circuitry 200 may be formed in and/or on a semiconductor substrate so as to underlie polyimide-based capacitive RH sensor 206. However, it will be understood that in other embodiments, one or more components of RH sensor system 200 may be coupled together as separate discrete components which may or may not be enclosed in a single package. For example, in one exemplary embodiment, active circuitry of RH sensor system 200 may be integrated within a single semiconductor integrated circuit chip 290 that is in turn operatively coupled to a separate discrete polyimide-based capacitive RH sensor 206.

Figure 1:
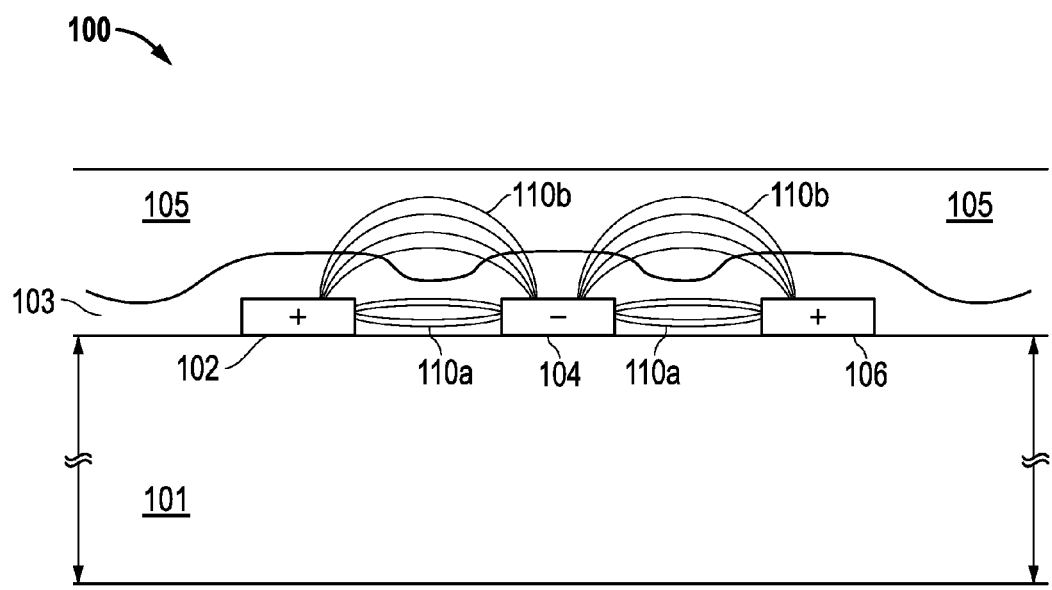
FIG. 1 illustrates a cross-section of a conventional capacitive sensor that is used for measuring relative humidity.

Still referring to FIG. 2, polyimide-based capacitive RH sensor 206 may include a polyimide-based sensing structure (e.g., a polyimide layer or other suitable material configuration) and interdigitated "finger" structures, or any other configuration of multiple capacitor plates separated by dielectric material that is suitable for forming a humidity-sensitive capacitor structure, e.g., such as parallel plate capacitor configurations. For example, in one exemplary embodiment capacitive sensor 206 may be a capacitive sensor 100 such as illustrated in FIG. 1 that includes sensor electrodes 102, 104 and 106 formed on substrate 101, with the electrodes covered by a dielectric passivation layer 103 and further overlaid with a polyimide sensing layer 105. However, in other embodiments any other type of dielectric material that absorbs water and exhibits a change in dielectric constant as a result thereof may be employed for a sensing material of a capacitive RH sensor or other type of RH humidity sensor that measures changes in other types of electrical parameters (e.g., such as effective resistance) as a function of changing dielectric constant. Examples of other such dielectric sensing materials include, but are not limited to, polyimides as well as non-polyimide polymers like acrylic polymers, polycarbonates, silicon based polymers such as polysiloxanes, etc.

In another exemplary embodiment, polyimide sensing layer 105 of FIG. 1 may be utilized without the inclusion of a passivation layer 103 such that sensor electrodes 102, 104 and 106 are directly covered and separated by polyimide material (or other type of suitable dielectric sensing layer material that replaces polyimide sensing layer 105 in other embodiments). Further information on example suitable capacitor sensor structures for use with the disclosed systems and methods may be found, for example, in U.S. Pat. No. 8,007,167; United States Patent Application Publication 2014/0026642; and United States Patent Application Publication 2014/0026653, the disclosure of each of the foregoing references being expressly incorporated herein by reference in its entirety for all purposes.

Still referring to FIG. 2, dielectric sensing material-based capacitive RH sensor 206 of RH sensor system 200 is coupled via analog-to-digital converter (ADC) 208 to provide a sensed digital capacitance value signal 226 (or other humidity-sensitive electrical parameter value signal in other embodiments) to a processing device 214 (e.g., microcontroller). For example, processing device 214 may be configured to execute RH calculation logic 218 to sense real time capacitance value of RH sensor 206 from signal 226 as the dielectric constant of polyimide sensing layer 105 changes with differing concentrations of water vapor in ambient gas (e.g., air) that contacts RH sensor 206. Non-volatile memory 220 coupled to processing device 214 may also be present for storing programming logic as well as look up tables and/or other data to support operation of processing device 214.

As shown, RH sensor system 200 may also include a temperature sensor 210 coupled to processing device 214 via ADC 212. In this embodiment, temperature sensor 210 is configured to sense real time operating temperature of RH sensor 206 and to provide the sensed real time temperature value as a digital temperature signal 228 to RH calculation logic 218 or processing device 214, which may be configured to in turn utilize the sensed temperature of RH sensor 206 to correct the sensed capacitance value of RH sensor 206 for temperature effects. Although illustrated as a microcontroller in this embodiment, it will be understood that any other type of processing device (e.g., controller, CPU, FPGA, ASIC, CPLD, etc.) that is suitable for performing the described tasks of processing device 214 may be alternatively employed in other embodiments.

As further shown in FIG. 2, RH sensor system 200 also includes variable frequency generator 202 (e.g., voltage controlled oscillator "VCO") that may be controlled by frequency control logic 216 executed by processing device 214 to provide a controllable and variable frequency measurement signal 225 to dielectric sensing material-based capacitive RH sensor 206, in this case coupled in parallel to phase angle measurement sensor 204. Variable frequency generator 202 may be any circuitry suitable for producing variable Frequency measurement signal 225 at a selected frequency that is controlled by frequency control signal 222 provided by frequency control logic 216 of processing device 214. Phase angle measurement sensor 204 may be any circuitry that is suitable for sensing the real time phase angle of measurement signal 225 and to provide a digital phase angle signal 224 representative of this real time sensed phase angle to RH calculation logic 218 of processing device 214 as shown. Examples of phase angle measurement sensor 204 include, but are not limited to, integrated circuitry that is configured with phase angle measurement circuit components of a vector impedance analyzer, network analyzer, LCR meter, etc.

In an alternative embodiment, it is possible that an additional second phase angle measurement sensor may be optionally coupled between dielectric sensing material-based capacitive RH sensor 206 and ADC 208 and may use any circuitry that is suitable for sensing the real time phase angle of a humidity dependent capacitor signal between RH sensor 206 and ADC 208 and for providing a second digital phase angle signal representative of this real time sensed humidity dependent phase angle to RH calculation logic 218 of processing device 214. In such an alternative embodiment, RH calculation logic 218 of processing device 214 may calculate the difference in phase angle between RH sensor 206 and ADC 208 (or between the reference path and the humidity dependent capacitor path) for use as the real time sensor circuit phase angle in the sensor correction techniques described further herein.

While not wishing to bound by theory, it is believed that dielectric sensing material-based capacitors develop a frequency dependent loss term after exposure to high humidity, e.g., a resonant frequency past which the rotation of the polar molecule is 90 degrees out of phase with the applied oscillating E-field, resulting in a decrease in dielectric constant (peak in dielectric loss). In the case of polyimide-based capacitors, this loss is maximized when the excitation frequency is near the natural resonance of the diamine portion of the polyimide chain. If the test frequency is near this resonance the loss is a sensitive function of the amount of high humidity exposure the capacitor has seen. Moreover, the phase angle of the capacitance represents a loss term. As will be described further herein, processing device 214 may in one embodiment be configured to control the operation frequency of measurement signal 225 to optimize or otherwise improve accuracy of RH measurement from capacitive RH sensor 206, e.g., according to frequency control data stored in NV memory 220. In another embodiment, processing device 214 may additionally or alternatively be configured to vary the frequency of measurement signal 225 for test or calibration purposes, e.g., to allow measurement of phase angle at different frequencies as will be described further herein.

Figure 3:
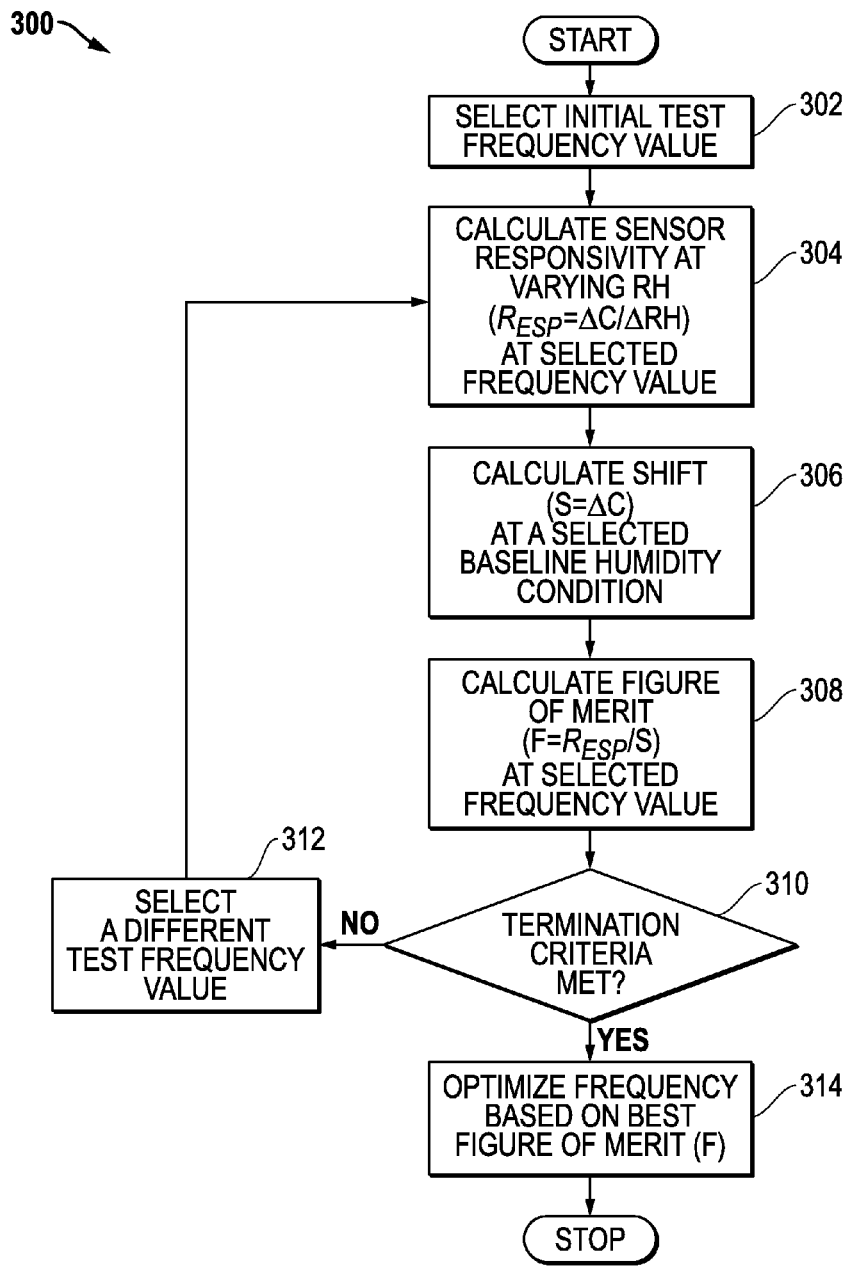
FIG. 3 illustrates methodology according to one exemplary embodiment of the disclosed systems and methods.

FIG. 3 illustrates one exemplary embodiment of an iterative characterization methodology 300 that may be implemented (e.g., in a test laboratory) to select an optimal operating frequency of signal (e.g., measurement signal 225 of FIG. 2) for use with a given design or configuration (e.g., given combination of material composition and structure) of dielectric sensing material-based capacitive RH sensor 206 to measure RH conditions. Methodology 300 is described below in terms of a capacitive RH sensor embodiment that employs capacitance as a humidity-sensitive electrical parameter value. However, it will be understood that methodology 300 may be similarly implemented in other embodiments with RH sensors that employ other types of humidity-sensitive electrical parameters that are suitable for use to sense changes in dielectric constant of a sensor dielectric material (e.g., such as effective resistance), in which case measurement of another type of humidity-sensitive electrical parameter may be substituted for capacitance in the steps of methodology 300 of FIG. 3.

As shown, methodology 300 begins with step 302 where an initial test frequency value is selected. An initial test frequency value may be selected in any suitable manner, for example, by beginning at the bottom of a defined frequency range (in which case subsequent iterations may be performed at successively higher frequency values until a top of the defined frequency range is reached), or by beginning at the top of a defined frequency range (in which case subsequent iterations may be performed at successively lower frequency values until a bottom of the defined frequency range is reached).

Figure 4:
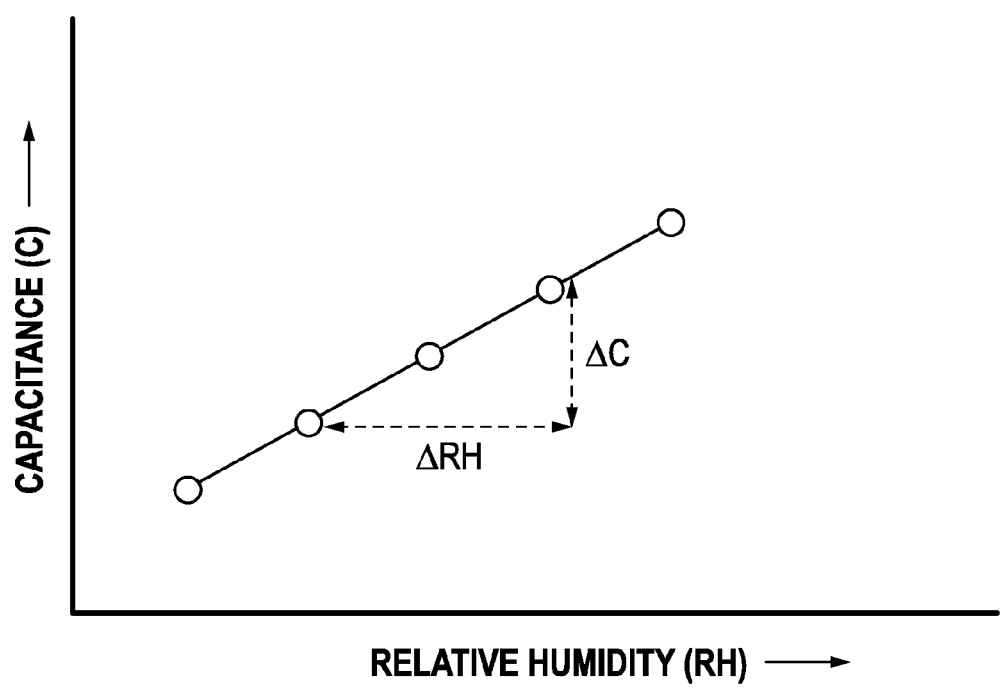
FIG. 4 illustrates capacitance versus relative humidity according to one exemplary embodiment of the disclosed systems and methods.

Next, in step 304, sensor responsivity $R_{ESP}$ is determined at varying levels of relative humidity (e.g., in a humidistat) for the current selected value of signal frequency at a selected constant sensor temperature, e.g., such as room temperature (23° C.) or other suitable constant temperature (such as 30° C.). FIG. 4 illustrates a hypothetical example plot of capacitance versus relative humidity such as may be obtained in step 304. Although step 304 may be performed using as few as two different relative humidity values, capacitance values (C) may be obtained at more than two levels of relative humidity in order to improve accuracy as shown, and the resulting data may be curve fitted if not linear, e.g., using least squares or other suitable curve fitting methodology. Responsivity ($R_{ESP}$) at the current selected signal frequency may be calculated in step 304 as the slope (e.g., $\Delta C/\Delta RH$) of the resulting linear relationship of FIG. 4 as shown. In other embodiments, responsivity ($R_{ESP}$) may be determined as the slope of any other measured humidity-sensitive electrical parameter (e.g., such as effective resistance) versus change in relative humidity values to which the RH sensor under test is exposed.

Figure 5:
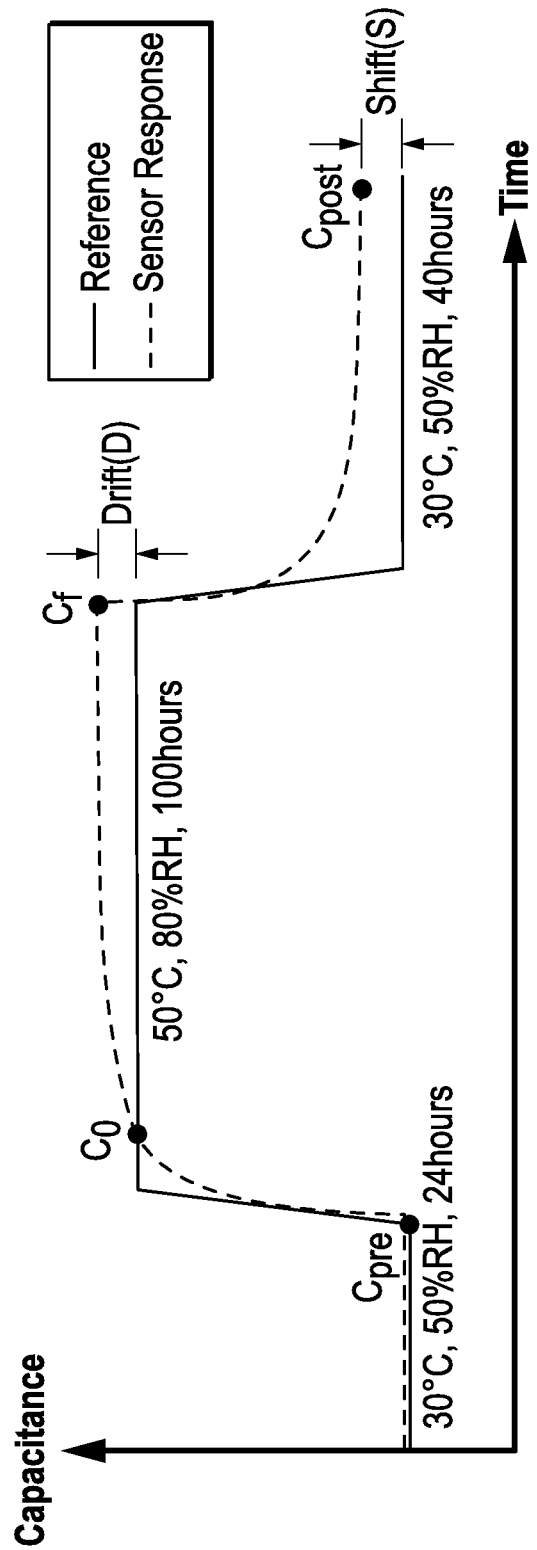
FIG. 5 illustrates a temperature sensor aging profile according to one exemplary embodiment of the disclosed systems and methods.

Next, in step 306 a value of shift (S) may be calculated relative to a reference capacitance value at selected baseline conditions of RH value and sensor temperature for a dielectric sensing material-based capacitive sensor that has been aged over time according to a prescribed RH and temperature sensor aging profile, e.g., in a humidistat. In this example, the reference value (solid line) at any given combination of RH and temperature may be set to be equal to the capacitance value (e.g., empirically measured) that would be exhibited by the dielectric sensing material-based capacitive sensor at the same combination of temperature and RH when the sensor is in an unaged condition (e.g., with no prior exposure to humidity or temperature that exceeds given baseline conditions of temperature and RH). FIG. 5 illustrates a hypothetical example of such a temperature sensor aging profile in which the unaged dielectric sensing material-based capacitive sensor is first exposed to baseline conditions (50% relative humidity at 30° C. for 24 hours in this example) during which negligible sensor shift (S) is exhibited. It will be understood that any suitable baseline conditions may be selected, e.g., such as typical ambient room-temperature/humidity conditions. Moreover, in one embodiment pre-exposure phase angle may be measured after any combination of exposure humidity value and exposure time that results in sensor shift and/or sensor drift values of less than or equal to about 10%, alternatively less than or equal to about 5%, and further alternatively less than about 1% of the original unaltered measured humidity-sensitive electrical parameters of a dielectric sensing material.

The exemplary temperature sensor aging profile of FIG. 5 includes next exposing the dielectric sensing material-based capacitive sensor to conditions of temperature and RH that are elevated above the baseline conditions (80% relative humidity at 50° C. for 100 hours in this example) during which sensor drift (D) may be observed as indicated in FIG. 5, followed by a return to the baseline conditions of 50% relative humidity at 30° C. for 24 hours which is a selected period of time to allow the observed value of capacitance to stabilize as shown. After the combined temperature sensor aging profile time of 148 hours, a value of shift (S) may be calculated for the current iteration of step 306. In alternative embodiments, a value of D may additionally or alternatively be calculated and employed in a similar manner as S value and used to optimize measurement frequency by selecting a frequency value that results in a smallest value of S and/or D. It will be understood that the temperature sensor aging profile of FIG. 5 is exemplary only and that any other combination of RH levels and/or time periods may be employed that are suitable for measuring S and/or D, and for allowing optimization of measurement frequency by selecting a frequency value that results in a smallest value (or alternatively a relative smaller value) of S and/or D.

Next, in step 308, a figure of merit (F) may be calculated for the current iteration of methodology 300 from the ratio of the current responsivity value ($R_{ESP}$) calculated in this iteration of step 304 to the current shift value (S) calculated in this iteration of step 306, i.e., $F=R_{ESP}/S$. It will be understood in an alternative embodiment, a value of drift (D) may be calculated relative to a reference capacitance value at selected elevated conditions of RH value and sensor temperature for a dielectric sensing material-based capacitive sensor that has been aged over time according to a prescribed RH and temperature sensor aging profile (e.g., see FIG. 5), and then figure of merit (F) values may be calculated for the current iteration of methodology 300 from the ratio of the current responsivity value ($R_{ESP}$) calculated in this iteration of step 304 to the current drift value (D) calculated in this iteration of step 306, i.e., $F=R_{ESP}/D$.

Methodology 300 then proceeds to step 310 where it is determined in step 310 whether termination criteria have been met. For example, methodology 300 may be iteratively performed for a selected number of different frequency values, in which case termination criteria of step 310 would be met when steps 304-308 have been performed for all of the selected number of different frequency values. If termination criteria are determined not to be met in current step 310, then methodology 300 proceeds to step 312 where a different test frequency is selected before methodology 300 returns to step 304 and repeats. Once termination criteria are found satisfied in step 310, then methodology 300 proceeds to step 314 where a signal frequency within the capability of the sensor electronics and corresponding to the best (e.g., highest) figure of merit value (F) may be selected as the optimum operating frequency of signal (e.g., measurement signal 225 of FIG. 2) to employ for use in measuring RH with the given configuration of a dielectric sensing material-based capacitive RH sensor, such as RH sensor 206 of system 200 of FIG. 2. For example, the value of optimum operating frequency from step 314 may be stored as frequency control data in non-volatile memory 220 that is read by frequency control logic 216 of processing device 214 during normal sensor operation. In yet another alternative, embodiment, steps 304 and 308 may be omitted, and optimum operating frequency may be iteratively selected by choosing an operating frequency in step 314 that yields the lowest value of shift (S) or drift (D), respectively, i.e., without calculation or consideration of figure of merit (F).

It will be understood that in one exemplary embodiment methodology 300 may be optionally performed multiple times during RH sensor characterization, e.g. to optimize signal frequency for different baseline and elevated conditions of humidity and/or temperature and/or time. Results of these multiple different frequency optimization runs may be optionally stored in a look up table or other suitable data format, e.g., that may be stored in non-volatile memory 220 and accessed by frequency control logic 216 of processing device 214 to select a given optimum frequency that corresponds most closely to recorded historic operation conditions of a given capacitive sensor 206. For example, during operation of system 200, processing device 214 may optionally track, record and store measured RH and/or sensor temperature values as a function of cumulative sensor operating time as frequency control data in non-volatile memory 220. Frequency control logic 216 of processing device 214 may then be optionally configured to select the optimum signal frequency for measured test conditions of RH, temperature and/or time that most closely corresponds to the current recorded historic (e.g., cumulative) sensor operating conditions of the given capacitive sensor 206. However, it will be understood that in other embodiments processing device 214 may be unaware of historic or cumulative sensor operating conditions (e.g., such as when the sensor is unpowered) and not store any such historic RH or sensor temperature values. Instead processing device 214 may employ a single preselected optimized higher frequency signal for capacitive measurements (e.g., to reduce drift and/or shift), and may measure and employ sensor circuit phase angle as a correction for drift error to the sensor reading as shown and described below in relation to FIG. 7. It is also possible in another embodiment, that a first selected signal frequency may be employed to measure capacitance change for RH determination, while another and different second signal frequency may be employed for measuring phase angle or resistance change for purpose of compensating for sensor drift.

It will also be understood that the illustrated steps of methodology 300 are exemplary only, and that any combination of fewer, additional, and/or other steps may be employed that are suitable for selecting an optimum operating frequency of signal (e.g., measurement signal 225 of FIG. 2) to employ for use in measuring RH. For example, in one alternative embodiment, steps 304 and 308 may be omitted and only step 306 performed to calculate shift (or drift) at a selected base line humidity condition. In such an alternative embodiment, step 312 may be performed to select a signal frequency within the capability of the sensor electronics and corresponding to the best (e.g., lowest) value of shift (or drift) as the optimum operating frequency of signal (e.g., measurement signal 225 of FIG. 2) to employ for use in measuring RH.

Figure 6A:
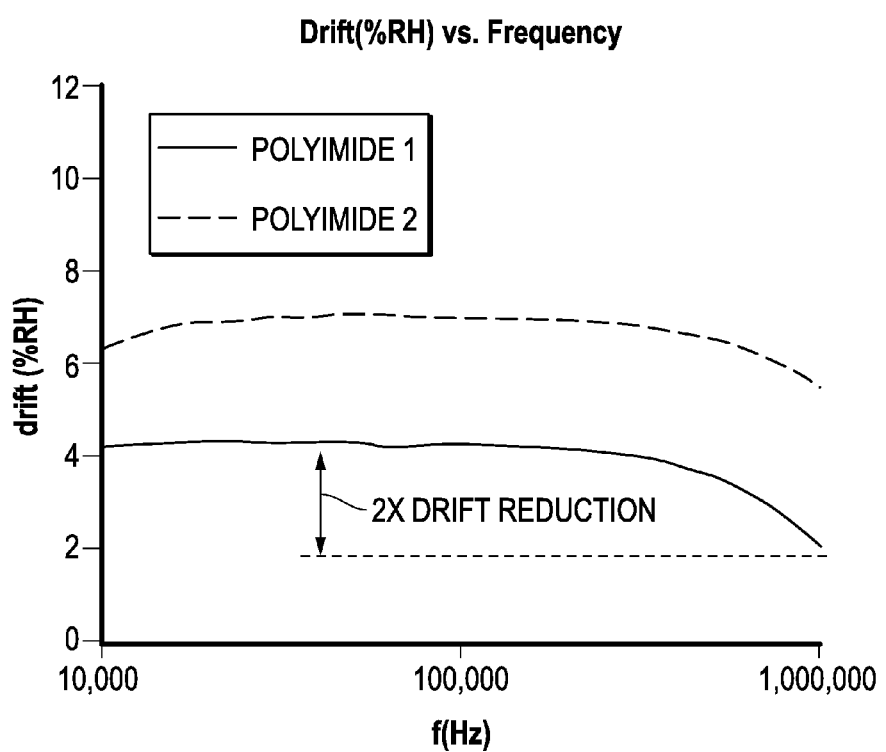
FIG. 6A illustrates polyimide-based relative humidity drift error as a function of measurement frequency according to one exemplary embodiment of the disclosed systems and methods.
Figure 6B:
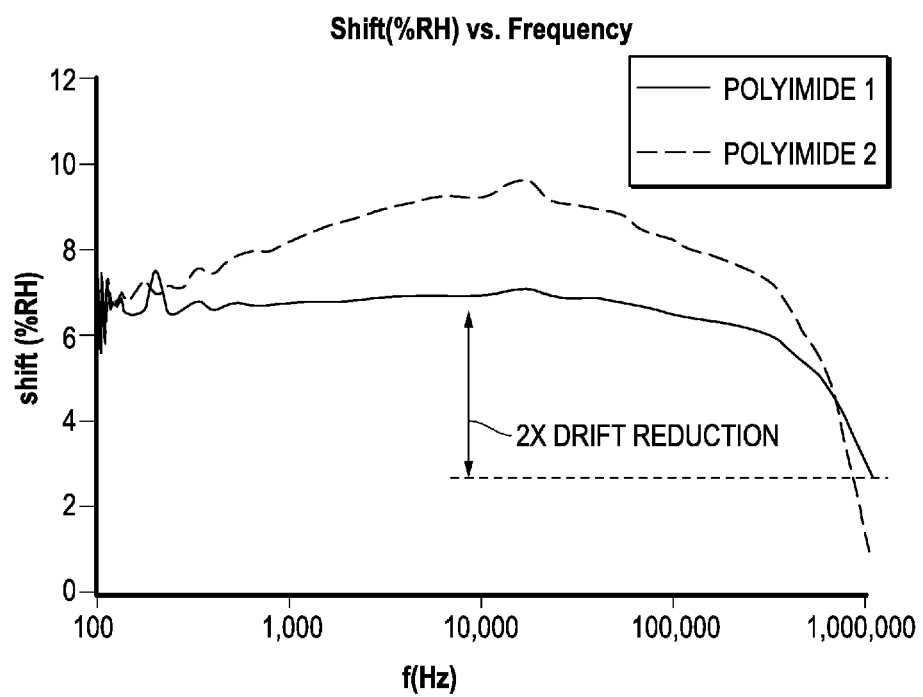
FIG. 6B illustrates polyimide-based relative humidity shift error as a function of measurement frequency according to one exemplary embodiment of the disclosed systems and methods.

FIG. 6A illustrates the effect of measurement frequency on observed PI drift error after sensor aging, it being understood that a similar relationship may be measured for PI shift as illustrated in FIG. 6B. To obtain the data of FIGS. 6A and 6B, frequency-dependent capacitive response to changes in RH was measured using test devices to evaluate polyimide shift and drift parameters at different operation frequencies for two different types of polyimide after 100 hours of exposure to conditions of 50° C. and 80% RH. The devices tested were of a simple, parallel-plate capacitive structure, with the given polyimide dielectric sandwiched between two aluminum electrodes. The top electrode was perforated to allow water vapor to enter the sensor. As shown in FIGS. 6A and 6B, drift and shift errors may be reduced by operating a dielectric sensing material-based capacitive RH sensor at higher frequencies (e.g., in this case by a factor of two at 1,000,000 Hz). Thus, in an alternative embodiment, relationship of calculated sensor drift and/or shift (e.g. such as may be calculated in the manner described in relation to FIG. 5) may be utilized directly (i.e., as an alternative to the figure of merit (F) of FIG. 3) to select an optimum operating frequency within the capability of the sensor electronics that minimizes drift and/or shift to employ for use in measuring RH with a given configuration of a dielectric sensing material-based capacitive RH sensor.

In another exemplary embodiment, the amount of drift (D) and/or shift (S) exhibited by a given dielectric sensing material-based capacitive RH sensor (e.g., due to sensor aging at higher humidities) may be characterized (e.g., in a test laboratory) as a function of sensor circuit phase angle $\phi$ measured for a given RH sensor design or configuration, e.g., using a laboratory vector impedance analyzer or using phase angle measurement sensor 204 of system 200 of FIG. 2. In this regard, evolution of a combination of series and/or parallel resistive component upon high RH exposure causes a permanent change in sensor circuit phase angle $\phi$ that may be measured and utilized in one exemplary embodiment as a correction for drift error to the sensor reading as shown and described below in relation to FIG. 7. Any frequency-based methods of measuring dielectric constant may be utilized on-chip or off-chip in the practice of the disclosed systems and methods to measure sensor circuit phase angle $\phi$ and to improve RH sensor performance, e.g., such as LCR meter, vector impedance analyzer, network analyzer, etc. instead. In another embodiment, effective resistance may be measured by making time domain measurement of the charging and discharging characteristics of sensor dielectric constant.

An un-aged polyimide sensor possesses a $\phi$ that is near −90°, i.e., that of an ideal capacitor. Although not wishing to be bound by theory, when the polyimide of the capacitive RH sensor is subjected to high humidity and temperature, swelling of the polyimide, water-trapping, and/or hydrolysis occur. This results in an increase in capacitance after high humidity exposure that does not reverse quickly and can be mistaken for a humidity increase. These material changes also manifest themselves in the form of a resistive path in the circuit model of the sensor. The once-ideal capacitive model now includes a resistive component, which shifts the phase angle away from −90°. This change in $\phi$ may be measured and used in one embodiment as an indicator of RH capacitive sensor aging. Based on how much $\phi$ has deviated from the pre-exposure (e.g., un-aged) value (this difference expressed here as $\Delta\phi$), a calculation may be applied to the inaccurate raw RH measurement to return a corrected value, e.g., by subtracting the indicated value of drift as a RH correction factor (X) obtained from the Y-axis from the inaccurate raw RH measurement. It will be understood that a similar relationship may be established for shift error. Such a $\phi$-based correction may be applied alone, or in combination with optimized (e.g., higher) measurement frequency such as described in relation to FIG. 6A. When employed together $\phi$-based correction using a correction factor X may be employed to achieve additional improvement in sensor accuracy over use of higher or optimized measurement frequency alone.

Figure 7:
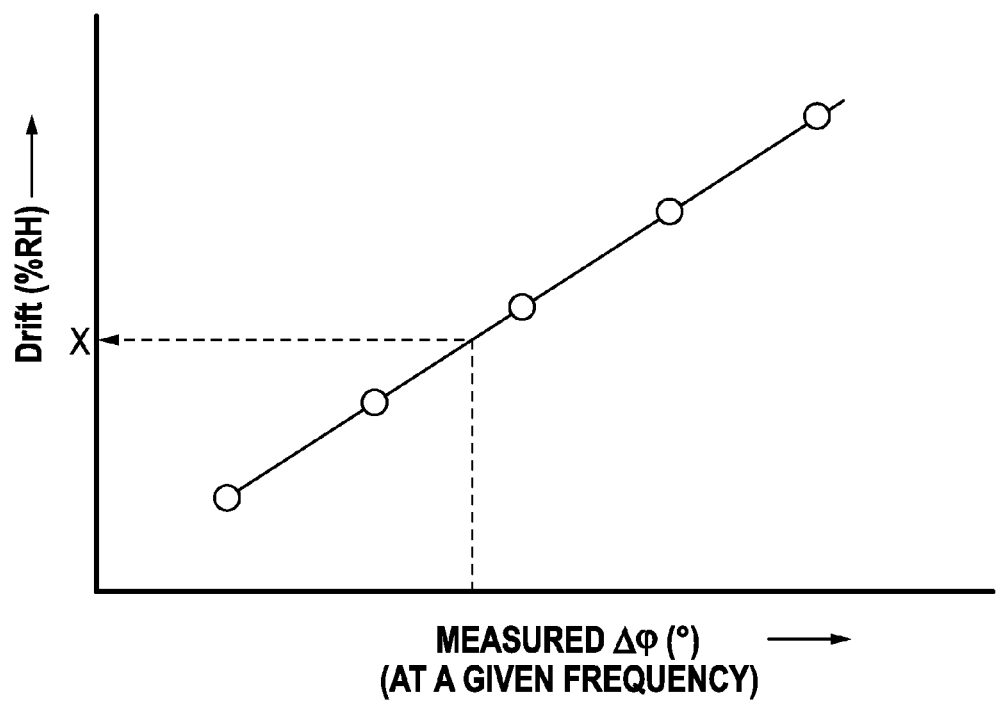
FIG. 7 illustrates polyimide-based relative humidity drift correction factor (X) as a function of change in phase angle ($\Delta\phi = \phi_{pre-exposure} - \phi_{post-exposure}$) according to one exemplary embodiment of the disclosed systems and methods.

In the exemplary embodiment of FIG. 7, values of $\Delta\phi=\phi_{pre-exposure}-\phi_{post-exposure}$ have been calculated at a given selected sensor operation frequency for a dielectric sensing material-based RH sensor, where each $\phi$ value for a given aged or unaged sensor is measured at the given same frequency and a given temperature (e.g., room temperature of 23° C. or other suitable constant temperature such as 30° C.). Such measurement may be made, for example, during device characterization in a laboratory environment using a vector impedance analyzer or using phase angle measurement sensor 204 of system 200 of FIG. 2. In the hypothetical example of FIG. 7, different measurements of $\phi$ and corresponding RH correction factor (X) have been made at the same frequency but at various increasing aging times (e.g., such as under aging conditions of 50° C. and 80% RH for an extended time period) for the given RH sensor. RH correction factor X may be, for example, the value of measured drift corresponding to calculated $\Delta\phi$ at a given frequency, which may be subtracted from the calculated raw RH value to correct the RH measurement and produce a corrected RH output signal. These measurements may be made during device characterization in a test laboratory or at any other suitable time. The resulting data may be used to generate a relationship between measured $\Delta\phi$ and drift such as illustrated in FIG. 7 that may be stored (e.g., in NV memory 220 of system 200) and later used (e.g., by RH calculation logic 218) as an indicator of the amount of prior high RH exposure and to correct or otherwise compensate the raw RH values obtained under operating conditions from a RH sensor system 200 deployed in the field. This relationship may be stored, for example, in NV memory 220 of RH sensor system 200, and then accessed as needed by RH calculation logic 218 of processing device 214.

After initial sensor device characterization such as described above, operational $\Delta\phi$ value may be later calculated using $\phi$ values measured during field operation of an aged RH sensor (e.g., measured by RH calculation logic 218 at the same given selected sensor operating frequency and under the same temperature conditions used during sensor characterization testing). Then, using the stored relationship of X versus $\Delta\phi$ of FIG. 7 (or other suitable relationship such as a look up table of RH correction factors X versus $\Delta\phi$ values), the raw RH value obtained from the RH sensor may be corrected by subtracting the RH correction factor X corresponding to the current operational $\Delta\phi$. For example, RH calculation logic 218 of RH sensor system 200 may be configured to receive real time phase angle $\phi$ values 224 during field operation of sensor system 200 from phase angle measurement sensor 204, calculate the current value of $\Delta\phi$, then access relationship of X versus $\Delta\phi$ that is stored on NV memory 220 to determine the corresponding RH correction factor C. In this example, RH calculation logic 218 of RH sensor system 200 may then calculate a RH output signal 230 that is corrected for aging by subtracting the value of correction factor X from the raw RH value that is calculated directly from the sensed digital capacitance value signal 226. It will be understood that sensor circuit phase angle $\phi$ may be continuously measured during field operation of an aged RH sensor, or may alternatively be measured at any interval of time (e.g., periodically) that is suitable for achieving a desired RH signal correction accuracy versus time. In one embodiment, longer time intervals (e.g., such as about one hour time interval) between phase angle $\phi$ measurements may be employed to reduce sensor power consumption where needed. In the latter case, phase angle $\phi$ does not have to be measured every time RH is measured.

In a further exemplary embodiment, a RH correction factor X (e.g., obtained from FIG. 7) may be further modified to account for higher real time current measured operating RH value. This is because more sensor aging effect is seen at higher measured humidity values, i.e., the change in capacitance due to aging after high humidity exposure is greater at relatively higher current measured values of humidity than at relative lower current measured values off humidity. Thus, in this embodiment the larger the measured humidity is, the larger is the correction factor X that is applied to the raw RH humidity value to produce the RH output signal.

Figure 8:
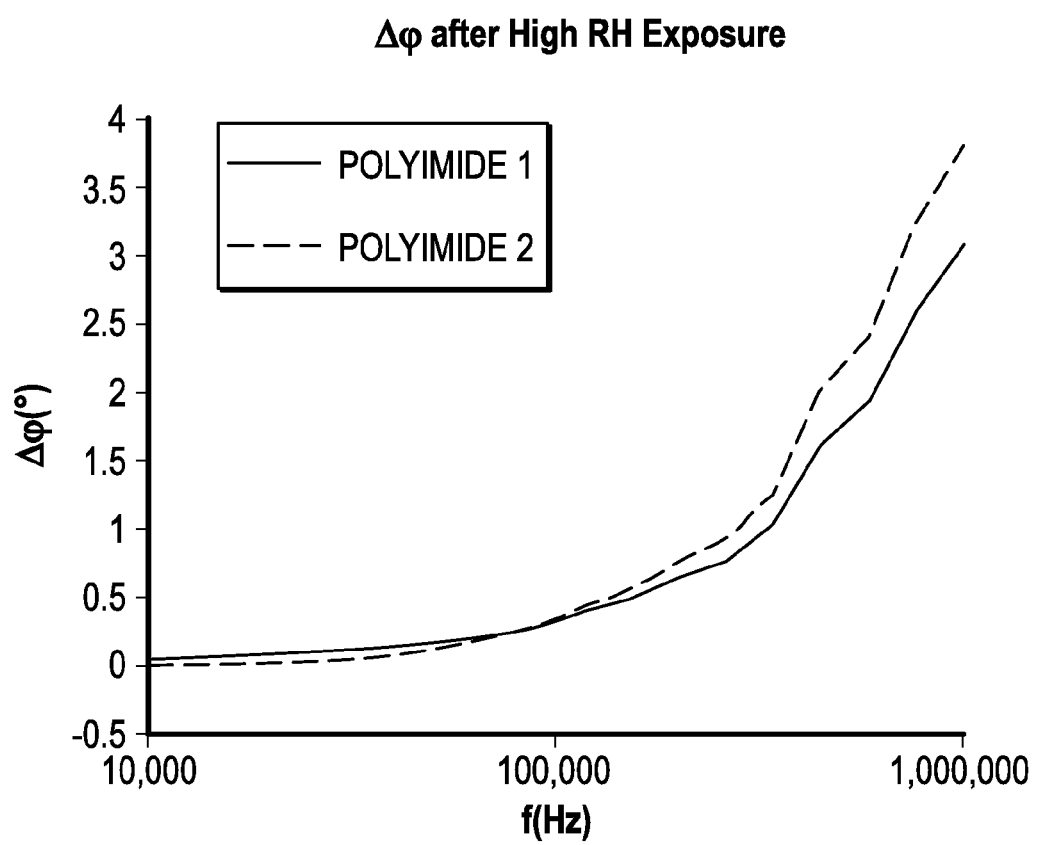
FIG. 8 illustrates frequency-dependent $\Delta\phi$ response for a given amount of relatively humidity sensor aging according to one exemplary embodiment of the disclosed systems and methods.

FIG. 8 illustrates frequency-dependent $\Delta\phi$ response for a given amount of RH sensor aging as measured using the same test device configuration and conditions as described above for FIG. 6A, e.g., $\phi$ values were measured and the resulting Δϕ values were calculated at different operation frequencies for the same two different types of polyimide after 100 hours of exposure to conditions of 50° C. and 80% RH. As illustrated in FIG. 8, Δϕ may be more accurately measured using relatively higher sensor frequencies since the value of the Δϕ response tends to be larger at higher frequencies. When taken together with the relatively lower values of drift error seen at higher sensor measurement frequencies, improved measurements of both raw RH value and Δϕ may be obtained using relatively higher frequencies in this embodiment. However, it will be understood that it is alternatively possible that in other embodiments a measurement frequency that results in the lowest value of drift error may be different than a measurement frequency that results in the largest measured Δϕ for the same sensor aging, temperature and RH conditions. Thus, it is possible in one embodiment to employ a different measurement frequency for measuring the raw RH value than is use for measuring ϕ during sensor operation. A processing device, such as processing device 214 of FIG. 2, may be configured to perform separate measurements in this fashion at periodic times, e.g., during field sensor operation of system 200. In any case, higher optimized measurement frequency for measuring capacitance may be employed together with RH correction factor C, in one example to improve RH measurement accuracy by more than a factor of two.

In yet another possible embodiment, measurement of capacitance value (e.g., via digital capacitance value signal 226) and measurement of phase angle ϕ may be made at multiple frequencies to achieve more robust correction over process, temperature and types of high humidity exposure. For example, it is possible in one embodiment to read sensor ADC output signal 226 at a frequency that provides the highest signal gain, but also conduct measurements of phase angle and capacitance at other frequencies that are optimized for lowest drift and highest change in phase angle as a function of aging. If the gain ratio between two frequencies is known, then the reading may be corrected accordingly using data from all frequencies.

It will also be understood that one or more of the tasks, functions, or methodologies described herein (e.g., including those described herein for components 204, 214, 216, 218, etc.) may be implemented by circuitry and/or by a computer program of instructions (e.g., computer readable code such as firmware code or software code) embodied in a non-transitory tangible computer readable medium (e.g., optical disk, magnetic disk, non-volatile memory device, etc.), in which the computer program comprising instructions are configured when executed (e.g., executed on one or more processing device such as CPU, controller, microcontroller, processor, microprocessor, FPGA, ASIC, or other suitable processing device) to perform one or more steps of the methodologies disclosed herein. In one embodiment, such processing devices may selected from the group consisting of CPU, controller, microcontroller, processor, microprocessor, FPGA, and ASIC. A computer program of instructions may be stored in or on the non-transitory computer-readable medium accessible by the processing device/s for instructing the processing device/s to execute the computer program of instructions. The computer program of instructions may include an ordered listing of executable instructions for implementing logical functions. The executable instructions may comprise a plurality of code segments operable to instruct the processing device/s to perform the methodology disclosed herein. It will also be understood that one or more steps of the present methodologies may be employed in one or more code segments of the computer program. For example, a code segment executed by the processing device/s may include one or more steps of the disclosed methodologies.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed systems and methods may be utilized in various combinations and/or independently. Thus the invention is not limited to only those combinations shown herein, but rather may include other combinations.

What is claimed is:

1. A method of operating a relative humidity (RH) sensor to measure RH conditions, the method comprising selecting an initial test measurement frequency as a current selected test measurement frequency for a humidity-sensitive dielectric material of the RH sensor; and then:
   a) exposing a humidity-sensitive dielectric material of the RH sensor to at least one value of RH while applying the current selected test measurement frequency to the humidity-sensitive dielectric material of the RH sensor;
   b) using at least one processing device to measure a humidity-sensitive electrical parameter value of the RH sensor at the exposed value of RH while applying the current selected test measurement frequency to the humidity-sensitive dielectric material of the RH sensor;
   c) using at least one processing device to determine a value of sensor shift (S) and/or sensor drift (D) at the current selected test measurement frequency by comparing the measured humidity-sensitive electrical parameter value to a baseline humidity-sensitive electrical parameter value previously measured at the same value of RH humidity;
   d) selecting at least one new and different test measurement frequency as the current selected test measurement frequency and iteratively repeating steps a) to d) for at least one additional time with the new current selected test measurement frequency; and then
   e) using at least one processing device to determine an operating humidity measurement frequency based at least in part on the values of S and/or D determined at previously-selected different test frequencies during multiple iterations of steps a) to d).

2. The method of claim 1, where the RH humidity sensor is a capacitive RH humidity sensor; where the humidity-sensitive electrical parameter value is a measured capacitance value; and where the baseline humidity-sensitive electrical parameter value is a baseline capacitance value.

3. The method of claim 1, further comprising performing step c) by using at least one processing device to determine either a value of sensor shift (S) or a value of sensor drift (D) at the current selected test measurement frequency by comparing the measured humidity-sensitive electrical parameter value to a baseline humidity-sensitive electrical parameter value previously measured at the same value of RH humidity; and performing step e) by using at least one processing device to select an operating humidity measurement frequency that corresponds to the test measurement frequency that produces the lowest value of S or D, respectively.

4. The method of claim 1, further comprising performing step a) of each iteration by exposing a humidity-sensitive dielectric material of the RH sensor to two or more different values of RH while applying the same current selected test measurement frequency to the humidity-sensitive dielectric material of the RH sensor; performing step b) of each iteration by using at least one processing device to measure a corresponding humidity-sensitive electrical parameter value of the RH sensor at each different respective exposed value of RH of step a) while applying the same current selected test measurement frequency to the humidity-sensitive dielectric material of the RH sensor; and using at least one processing device to perform the following additional steps for each iteration:

determining a value of sensor responsivity ($R_{ESP}$) at the current selected test frequency to be equal to a ratio of a change in measured humidity-sensitive electrical parameter values of the RH sensor during the current iteration of step b) to a change in corresponding different exposed values of RH to which the RH sensor is exposed during the current iteration of step a) while applying the same current selected test measurement frequency to the humidity-sensitive dielectric material;

determining a figure of merit (F) for the current iteration to be equal to a ratio of the current responsivity value ($R_{ESP}$) at the current selected test frequency to the value of sensor shift (S) or value of sensor drift (D) determined during the current iteration of step c) while applying the same current selected test measurement frequency to the humidity-sensitive dielectric material; and determining an operating humidity measurement frequency to be equal to the test frequency of the iteration having the largest corresponding figure of merit (F).

5. The method of claim 1, further comprising exposing the RH sensor to an atmosphere containing humidity after performing step e); and using at least one processing device to determine values of RH in the atmosphere based on values of humidity-sensitive electrical parameter values measured while applying the selected operating humidity measurement frequency of step e).

6. The method of claim 5, further comprising using at least one processing device to:

measure a pre-exposure phase angle ($\phi_{pre-exposure}$) of a circuit applying a given measurement frequency to the same or same type of humidity-sensitive dielectric material of the RH sensor prior to exposing the humidity-sensitive dielectric material of the RH sensor to the atmosphere after step e), the given measurement frequency being the same as or different from the operating humidity measurement frequency;

measure post-exposure phase angle ($\phi_{post-exposure}$) of a circuit applying a given measurement frequency to the humidity-sensitive dielectric material of the RH sensor after exposing the humidity-sensitive dielectric material of the RH sensor to some humidity present in the atmosphere;

determine a difference in the phase angle ($\Delta\phi$) between the pre-exposure phase angle ($\phi_{pre-exposure}$) and the post-exposure phase angle ($\phi_{post-exposure}$) of the circuit applying the given measurement frequency to the humidity-sensitive dielectric material; and then correct measured humidity-sensitive electrical parameter values of the RH sensor made at the selected operating humidity measurement frequency based on the determined difference in phase angle ($\Delta\phi$).

7. A method of operating a relative humidity (RH) sensor to measure RH conditions with a humidity-sensitive dielectric material of the RH sensor, the method comprising:

exposing a humidity-sensitive dielectric material of the RH sensor to a first humidity value while applying an operating humidity measurement frequency to the humidity-sensitive dielectric material of the RH sensor;

using at least one processing device to measure a humidity-sensitive electrical parameter value of the humidity-sensitive dielectric material while exposed to the first humidity value and while applying the operating humidity measurement frequency to the humidity-sensitive dielectric material of the RH sensor; and using at least one processing device to correct the measured humidity-sensitive electrical parameter value of the humidity-sensitive dielectric material based on a determined difference in phase angle phase angle ($\Delta\phi$) between a post-exposure phase angle ($\phi_{post-exposure}$) of a circuit applying a phase angle measurement frequency to the humidity-sensitive dielectric material and a predetermined pre-exposure phase angle ($\phi_{pre-exposure}$), the predetermined pre-exposure phase angle ($\phi_{pre-exposure}$) being measured prior to measurement of the post-exposure phase angle ($\phi_{post-exposure}$);

where the operating humidity measurement frequency and the phase angle measurement frequency are the same or different frequencies.

8. The method of claim 7, where the pre-exposure phase angle ($\phi_{pre-exposure}$) is a value determined from a circuit applying the phase angle measurement frequency to the same or same type of humidity-sensitive dielectric material of the RH sensor prior to exposing the humidity-sensitive dielectric material of the RH sensor to first humidity level; and where the method further comprises:

using at least one processing device to measure the current post-exposure phase angle ($\phi_{post-exposure}$) of a circuit applying the phase angle measurement frequency to the humidity-sensitive dielectric material of the RH sensor during or after exposing the humidity-sensitive dielectric material of the RH sensor to the first humidity level;

using at least one processing device to determine the difference in phase angle ($\Delta\phi$) between the current post-exposure phase angle ($\phi_{post-exposure}$) and the predetermined pre-exposure phase angle ($\phi_{pre-exposure}$); and then using at least one processing device to correct the measured humidity-sensitive electrical parameter value of the humidity-sensitive dielectric material while exposed to the first humidity value based on predetermined relationship between the determined difference in phase angle ($\Delta\phi$) and a value of shift (S) and/or drift (D).

9. The method of claim 8, where the pre-exposure phase angle ($\phi_{pre-exposure}$) is a value stored in non-volatile memory; where the predetermined relationship between the determined difference in phase angle ($\Delta\phi$) and a value of shift (S) and/or drift (D) is stored in non-volatile memory; and where the method further comprises using at least one processing device to:

retrieve the pre-exposure phase angle ($\phi_{pre-exposure}$) value from the non-volatile memory to determine the difference in phase angle ($\Delta\phi$) between the current post-exposure phase angle ($\phi_{post-exposure}$) and the predetermined pre-exposure phase angle ($\phi_{pre-exposure}$); and retrieve the predetermined relationship between the determined difference in phase angle ($\Delta\phi$) and a value of shift (S) and/or drift (D) to correct the measured humidity-sensitive electrical parameter value of the humidity-sensitive dielectric material based on the retrieved predetermined relationship.

10. The method of claim 7, where the operating humidity measurement frequency and the phase angle measurement frequency are different frequencies.

11. The method of claim 7, further comprising determining the predetermined pre-exposure phase angle ($\phi_{pre\text{-}exposure}$) from a circuit applying the phase angle measurement frequency to the humidity-sensitive dielectric material of a first RH sensor; and then:

operating a second RH sensor to measure RH conditions with a humidity-sensitive dielectric material of the second RH sensor, the humidity-sensitive dielectric material of the second RH sensor being the same type of material as the humidity-sensitive dielectric material of the first RH sensor;

exposing a humidity-sensitive dielectric material of the second RH sensor to a second humidity value while applying an operating humidity measurement frequency to the humidity-sensitive dielectric material of the second RH sensor;

using at least one processing device to measure a humidity-sensitive electrical parameter value of the humidity-sensitive dielectric material of the second RH sensor while exposed to the first humidity value and while applying the operating humidity measurement frequency to the humidity-sensitive dielectric material of the second RH sensor; and using at least one processing device to correct the measured humidity-sensitive electrical parameter value of the humidity-sensitive dielectric material of the second RH sensor based on a determined difference in phase angle phase angle ($\Delta\phi$) between a post-exposure phase angle ($\phi_{post\text{-}exposure}$) of a circuit applying a phase angle measurement frequency to the humidity-sensitive dielectric material of the second RH sensor and the predetermined pre-exposure phase angle ($\phi_{pre\text{-}exposure}$);

where the first and second RH sensors are different RH sensor devices.

12. A semiconductor circuit device, comprising at least one processing device configured to be coupled to a humidity-sensitive dielectric material of a relative humidity (RH) sensor, the processing device being programmed to receive and measure a humidity-sensitive electrical parameter value signal that is produced from the humidity-sensitive dielectric material in response to application of a humidity measurement frequency to the humidity-sensitive dielectric material, and to produce a relative humidity (RH) output signal based on the humidity-sensitive electrical parameter value signal, the RH output signal being representative of a value of RH to which the humidity-sensitive dielectric material is currently exposed; and where the processing device is further programmed to:

a) measure a humidity-sensitive electrical parameter value of the RH sensor at an exposed value of RH while a current selected test measurement frequency is applied to the humidity-sensitive dielectric material of the RH sensor;

b) determine a value of sensor shift (S) and/or sensor drift (D) at the current selected test measurement frequency by comparing the measured humidity-sensitive electrical parameter value to a baseline humidity-sensitive electrical parameter value previously measured at the same value of RH humidity;

c) iteratively repeat steps a) and b) for at least one additional time at a new current selected test measurement frequency that is different from the previous current selected test measurement frequency; and then d) determine an operating humidity measurement frequency based at least in part on the values of S and/or D determined at previously-selected different test frequencies during multiple iterations of steps a) and b).

13. The device of claim 12, further comprising:
a humidity-sensitive dielectric material that is coupled to the processing device;
a variable frequency generator coupled to provide a controllable and variable frequency measurement signal to the humidity-sensitive dielectric material, the processing device being coupled to control the frequency of the measurement signal; and
non-volatile memory coupled to the processing device, the processing device being programmed to store the determined operating humidity measurement frequency in the non-volatile memory and to later retrieve the store determined operating humidity measurement frequency from the nonvolatile memory.

14. The device of claim 13, where the components of the device are integrated on a single semiconductor integrated circuit chip.

15. The device of claim 12, where the RH humidity sensor is a capacitive RH humidity sensor; where the humidity-sensitive electrical parameter value is a measured capacitance value; and where the baseline humidity-sensitive electrical parameter value is a baseline capacitance value.

16. The device of claim 12, where the processing device is further programmed to perform step b) determining either a value of sensor shift (S) or a value of sensor drift (D) at the current selected test measurement frequency by comparing the measured humidity-sensitive electrical parameter value to a baseline humidity-sensitive electrical parameter value previously measured at the same value of RH humidity; and to perform step d) by selecting an operating humidity measurement frequency that corresponds to the test measurement frequency that produces the lowest value of S or D, respectively.

17. The device of claim 12, where the processing device is further programmed to perform step a) of each iteration by measuring a corresponding humidity-sensitive electrical parameter value of the RH sensor at different respective exposed values of RH while the current selected test measurement frequency is applied to the humidity-sensitive dielectric material of the RH sensor; and to perform the following additional steps for each iteration:

determine a value of sensor responsivity ($R_{ESP}$) at the current selected test frequency to be equal to a ratio of a change in measured humidity-sensitive electrical parameter values of the RH sensor during the current iteration to a change in corresponding different exposed values of RH to which the RH sensor is exposed during the current iteration while the current selected test measurement frequency is applied to the humidity-sensitive dielectric material;

determine a figure of merit (F) for the current iteration to be equal to a ratio of the current responsivity value ($R_{ESP}$) at the current selected test frequency to the value of sensor shift (S) or value of sensor drift (D) determined during the current iteration of step b) while the current selected test measurement frequency is applied to the humidity-sensitive dielectric material; and determine an operating humidity measurement frequency to be equal to the test frequency of the iteration having the largest corresponding figure of merit (F).

18. The device of claim 12, where the processing device is further programmed to expose the RH sensor to an atmosphere containing humidity after performing step e); and using at least one processing device to determine values of RH in an atmosphere to which the RH sensor is exposed based on values of humidity-sensitive electrical parameter values measured while applying the selected operating humidity measurement frequency of step d).

19. The device of claim 18, where the processing device is further programmed to:
measure a pre-exposure phase angle ($\phi_{pre-exposure}$) of a circuit applying a given measurement frequency to the same or same type of humidity-sensitive dielectric material of the RH sensor prior to exposing the humidity-sensitive dielectric material of the RH sensor to the atmosphere after step e), the given measurement frequency being the same as or different from the operating humidity measurement frequency;
measure post-exposure phase angle ($\phi_{post-exposure}$) of a circuit applying the given measurement frequency to the humidity-sensitive dielectric material of the RH sensor after exposing the humidity-sensitive dielectric material of the RH sensor to some humidity present in the atmosphere;
determine a difference in the phase angle ($\Delta\phi$) between the pre-exposure phase angle ($\phi_{pre-exposure}$) and the post-exposure phase angle ($\phi_{post-exposure}$) of the circuit applying the given measurement frequency to the humidity-sensitive dielectric material; and
then correct measured humidity-sensitive electrical parameter values of the RH sensor made at the selected operating humidity measurement frequency based on the determined difference in phase angle ($\Delta\phi$).

20. A semiconductor circuit device, comprising at least one processing device configured to be coupled to a humidity-sensitive dielectric material of a relative humidity (RH) sensor, the processing device being programmed to receive and measure a humidity-sensitive electrical parameter value signal that is produced from the humidity-sensitive dielectric material in response to application of a measurement frequency to the humidity-sensitive dielectric material, and to produce a relative humidity (RH) output signal based on the humidity-sensitive electrical parameter value signal, the RH output signal being representative of a value of RH to which the humidity-sensitive dielectric material is currently exposed; and where the processing device is further programmed to:
measure a humidity-sensitive electrical parameter value of the humidity-sensitive dielectric material while exposed to a first humidity value and while applying an operating humidity measurement frequency to the humidity-sensitive dielectric material of the RH sensor;
measure a post-exposure phase angle ($\phi_{post-exposure}$) of a circuit applying a phase angle measurement frequency to the humidity-sensitive dielectric material;
determine a difference in phase angle phase angle ($\Delta\phi$) between a post-exposure phase angle ($\phi_{post-exposure}$) of a circuit applying a phase angle measurement frequency to the humidity-sensitive dielectric material and a predetermined pre-exposure phase angle ($\phi_{pre-exposure}$) that is measured prior to measurement of the post-exposure phase angle ($\phi_{post-exposure}$); and
correct the measured humidity-sensitive electrical parameter value of the humidity-sensitive dielectric material based on a determined difference in phase angle phase angle ($\Delta\phi$) between the post-exposure phase angle ($\phi_{post-exposure}$) and the predetermined pre-exposure phase angle ($\phi_{pre-exposure}$);
where the operating humidity measurement frequency and the phase angle measurement frequency are the same or different frequencies.

21. The device of claim 20, where the pre-exposure phase angle ($\phi_{pre-exposure}$) is a value determined from a circuit applying the phase angle measurement frequency to the same or same type of humidity-sensitive dielectric material of the RH sensor prior to exposing the humidity-sensitive dielectric material of the RH sensor to the first humidity level; and where the processing device is further programmed to:
measure the current post-exposure phase angle ($\phi_{post-exposure}$) of a circuit applying the phase angle measurement frequency to the humidity-sensitive dielectric material of the RH sensor during or after exposing the humidity-sensitive dielectric material of the RH sensor to the first humidity level;
determine the difference in phase angle ($\Delta\phi$) between the current post-exposure phase angle ($\phi_{post-exposure}$) and the predetermined pre-exposure phase angle ($\phi_{pre-exposure}$); and
correct the measured humidity-sensitive electrical parameter value of the humidity-sensitive dielectric material while exposed to the first humidity value based on predetermined relationship between the determined difference in phase angle ($\Delta\phi$) and a value of shift (S) and/or drift (D).

22. The device of claim 21, further comprising non-volatile memory coupled to the processing device; where the pre-exposure phase angle ($\phi_{pre-exposure}$) is a value stored in the non-volatile memory; where the predetermined relationship between the determined difference in phase angle ($\Delta\phi$) and a value of shift (S) and/or drift (D) is stored in the non-volatile memory; and where the processing device is further programmed to:
retrieve the pre-exposure phase angle ($\phi_{pre-exposure}$) value from the non-volatile memory to determine the difference in phase angle ($\Delta\phi$) between the current post-exposure phase angle ($\phi_{post-exposure}$) and the predetermined pre-exposure phase angle ($\phi_{pre-exposure}$); and
retrieve the predetermined relationship between the determined difference in phase angle ($\Delta\phi$) and a value of shift (S) and/or drift (D) to correct the measured humidity-sensitive electrical parameter value of the humidity-sensitive dielectric material based on the retrieved predetermined relationship.

23. The device of claim 20, where the operating humidity measurement frequency and the phase angle measurement frequency are different frequencies.

24. The device of claim 20, further comprising:
a humidity-sensitive dielectric material that is coupled to the processing device;
a frequency generator coupled to provide a frequency measurement signal to the humidity-sensitive dielectric material;
a phase angle measurement sensor coupled to the frequency generator and the humidity-sensitive dielectric material to measure the post-exposure phase angle ($\phi_{post-exposure}$); and
non-volatile memory coupled to the processing device, the pre-exposure phase angle ($\phi_{pre-exposure}$) being a value stored in the non-volatile memory, and the predetermined relationship between the determined difference in phase angle ($\Delta\phi$) and a value of shift (S) and/or drift (D) being stored in the non-volatile memory;

where the processing device is further programmed to retrieve the pre-exposure phase angle ($\phi_{pre-exposure}$) value from the non-volatile memory to determine the difference in phase angle ($\Delta\phi$) between the current post-exposure phase angle ($\phi_{post-exposure}$) and the pre-determined pre-exposure phase angle ($\phi_{pre-exposure}$); and to retrieve the predetermined relationship between the determined difference in phase angle ($\Delta\phi$) and a value of shift (S) and/or drift (D) to correct the measured humidity-sensitive electrical parameter value of the humidity-sensitive dielectric material based on the retrieved predetermined relationship.

25. The device of claim 24, where the components of the device are integrated on a single semiconductor integrated circuit chip.

* * * * *